United States Patent
Hansen

(10) Patent No.: US 11,201,031 B2
(45) Date of Patent: Dec. 14, 2021

(54) HIGH VOLTAGE SEALS AND STRUCTURES HAVING REDUCED ELECTRIC FIELDS

(71) Applicant: Varex Imaging Corporation, Salt Lake City, UT (US)

(72) Inventor: Wayne R. Hansen, Salt Lake City, UT (US)

(73) Assignee: Varex Imaging Corporation, Salt Lake City, UT (US)

( * ) Notice: Subject to any disclaimer, the term of this patent is extended or adjusted under 35 U.S.C. 154(b) by 92 days.

(21) Appl. No.: 15/928,141

(22) Filed: Mar. 22, 2018

(65) Prior Publication Data

US 2019/0295803 A1     Sep. 26, 2019

(51) Int. Cl.
| | |
|---|---|
| *H01J 35/16* | (2006.01) |
| *A61B 6/03* | (2006.01) |
| *G01N 23/083* | (2018.01) |
| *H01B 17/44* | (2006.01) |
| *H01J 5/26* | (2006.01) |
| *H01J 9/26* | (2006.01) |

(52) U.S. Cl.
CPC .............. *H01J 35/16* (2013.01); *A61B 6/035* (2013.01); *G01N 23/083* (2013.01); *H01B 17/44* (2013.01); *H01J 5/26* (2013.01); *H01J 9/26* (2013.01); *H01J 2235/163* (2013.01); *H01J 2235/165* (2013.01)

(58) Field of Classification Search
CPC .... H01J 1/52; H01B 1/24; H01B 3/12; H01G 9/042; H01G 9/155; H01G 4/10; H01G 4/12

See application file for complete search history.

(56) References Cited

U.S. PATENT DOCUMENTS

| | | | |
|---|---|---|---|
| 1,730,171 A | 7/1929 | Smith | |
| 1,969,911 A | 1/1931 | Smith | |
| 4,126,803 A | 11/1978 | Bader et al. | |
| 4,185,161 A | 1/1980 | Huang et al. | |
| 5,136,625 A * | 8/1992 | Heiting | H01J 35/16 |
| | | | 378/119 |
| 6,570,960 B1 * | 5/2003 | Kuzniar | H01J 35/101 |
| | | | 378/121 |

(Continued)

FOREIGN PATENT DOCUMENTS

| | | |
|---|---|---|
| DE | 10 2016 214752 A1 | 2/2018 |
| JP | 404248233 | 9/1992 |

OTHER PUBLICATIONS

EPO Search Report for Varex Imaging Corp.'s EP 19164354.3—1212 dated Aug. 26, 2019.

*Primary Examiner* — Kenneth J Malkowski
(74) *Attorney, Agent, or Firm* — Laurence & Phillips IP Law

(57) ABSTRACT

Some embodiments include a structure, comprising: an insulator forming at least a part of a wall of a vacuum chamber, the insulator having a first end and a second end wider than the first end; a first conductive structure disposed at the first end of the insulator; and a second conductive structure disposed at the second end of the insulator, contacting the insulator, and including at least a portion surrounded by the insulator; wherein: a portion of an outer surface of the insulator extends radially outward from a triple junction between the insulator, the second conductive structure, and a medium contacting the outer surface of the insulator.

18 Claims, 3 Drawing Sheets

(56) References Cited

U.S. PATENT DOCUMENTS

| | | | |
|---|---|---|---|
| 6,570,962 B1 | 5/2003 | Maska et al. | |
| 6,750,962 B2* | 6/2004 | Douglas | G01N 21/8483 356/246 |
| 6,901,136 B1* | 5/2005 | Tekletsadik | H01J 35/06 378/119 |
| 7,236,569 B2* | 6/2007 | Takeuchi | H01J 35/16 378/136 |
| 9,159,525 B2* | 10/2015 | Yamazaki | H01J 35/06 |
| 9,514,910 B2* | 12/2016 | Yanagisawa | H01J 35/20 |
| 2009/0285360 A1* | 11/2009 | Cao | H01J 35/16 378/98 |
| 2014/0269467 A1* | 9/2014 | Samanta Singhar | H04W 52/0225 370/311 |
| 2014/0291543 A1* | 10/2014 | Sato | H01J 37/3171 250/423 R |
| 2014/0369467 A1 | 12/2014 | Yamazaki et al. | |
| 2016/0126050 A1 | 5/2016 | Parashar | |
| 2017/0053771 A1* | 2/2017 | Jeong | H01J 35/065 |

\* cited by examiner

HIGH VOLTAGE SEALS AND STRUCTURES HAVING REDUCED ELECTRIC FIELDS

BACKGROUND

This disclosure relates to high voltage seals and structures having reduced electric fields.

High voltage enclosures such as vacuum tubes use ceramic insulators to offset a high voltage from a lower voltage. For example, an anode at a high voltage may be offset from a body of the vacuum tube by the ceramic insulator. The body of the vacuum tube is attached to ceramic insulator. A metallic seal ring may be brazed on to an outer surface of the ceramic insulator to attach the body to the ceramic insulator. This attachment creates a triple junction between the ceramic insulator, the seal ring, and a surrounding media. An electric field at this triple junction may be relatively high, resulting in electrons that may become the source of arcing and/or punctures.

DETAILED DESCRIPTION

As will be described in further detail below, in some embodiments, the seal on an insulator may be located on the inside diameter of an insulator. Locating the seal on the inside improves high voltage stability and manufacturability. For example, the location of the seal may decrease the electric field at both the inner and outer triple junctions formed by the seal, resulting in reduced electron movement, arcing, and punctures.

Figure 1:
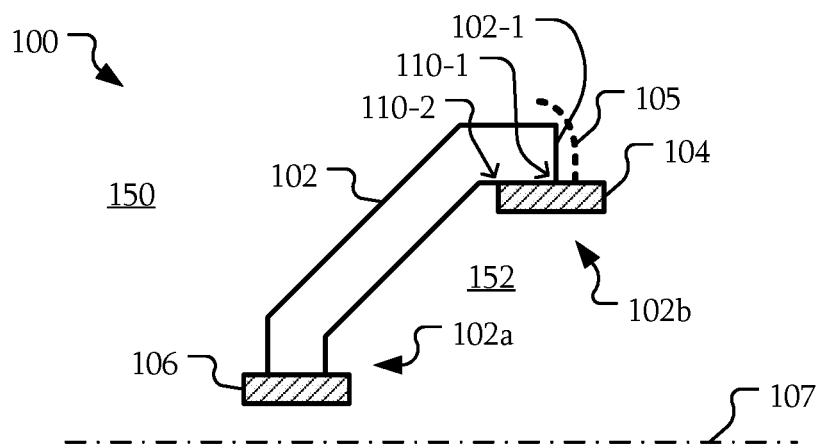
FIG. 1 is a cross-section of a wall of a high voltage structure according to some embodiments.

FIG. 1 is a cross-section of a wall of a high voltage structure according to some embodiments. As used herein, a high voltage structure is a structure that is coupled to a voltage difference greater than 50 kilovolts (kV) in some examples, greater than 100 kV in other examples, or greater than 150 kV in still other examples. The high voltage structure 100 includes an insulator 102. The insulator 102 may be a ceramic, glass, or the like. The insulator 102 includes a first end 102a and a second end 102b. The second end 102b is wider than the first end 102a. For example, a radial distance from the axis 107 to the second end 102b may be larger than the radial distance from the axis 107 to the first end 102a. The insulator 102 may be a high voltage insulator having a material and structure that can isolate conductive structures have a voltage difference greater than 50 kV, 100 kV, 150 kV, or the like.

A conductive structure 106 is disposed at the first end 102a of the insulator 102. The conductive structure 106 may be a seal ring configured to seal a chamber formed in part by the insulator 102. As will be described below, the conductive structure 106 may be electrically connected to an anode. Moreover, a voltage of the conductive structure 106 may be relatively high relative to the voltage on the second end 102b of the insulator 102. Relatively high indicates a voltage difference greater than 10 kV.

A conductive structure 104 is disposed at the second end 102b of the insulator 102. The conductive structure 104 may be a seal ring configured to seal a chamber formed in part by the insulator 102. The conductive structures 104 and 106 may include a conductive material, such as lead, nickel, steel, alloys of such materials or similar materials, or the like.

The conductive structure 104 contacts the insulator, forming two triple junctions 110-1 and 110-2. Although illustrated as points in this cross-section, the triple junctions 110 may have a circular shape on a conical insulator, a polygonal or elliptical shape on a frustum insulator, or another closed shape formed of linear and/or curved segments. The first triple junction 110-1 is formed between the insulator 102, the conductive structure 104, and a medium 150 contacting the outer surface of the insulator 102. For example, the medium 150 may be a gas (e.g., air, nitrogen, and argon), oil (e.g., dielectric oil, insulating oil, or glycol such as ethylene glycol or propylene glycol), a coolant, or the like. The second triple junction 110-2 is formed between an inner surface of the insulator 102, the conductive structure 104, and a medium 152 contacting the inner surface of the insulator 102. The medium may include a vacuum. Here, inner and outer are defined by the relationship of the high voltage structure 100 to the axis 107.

The conductive structures 104 and 106 may be attached to the insulator 102 in a variety of ways. For example, the conductive structures 104 and 106 may be attached through soldering, welding, brazing, compression, or the like. The conductive structures 104 and 106 may, but need not be attached to the insulator 102 using the same technique.

In some embodiments, a coronal shield 105 does not extend over the triple junction 110-1. That is, no coronal shield 105 is present to shield the triple junction 110-1. The coronal shield 105 is illustrated with dashed lines to illustrate the lack of such a coronal shield 105. In a particular example, the medium 150 contacting the outer surface of the insulator 102 may be oil. The triple junction 110-1 between the oil, the insulator 102, and the conductive structure 104 may not be shielded by a coronal shield 105. In addition, the triple junction 110-1 is further from the conductive structure 106 than the triple junction 110-2 and the conductive structure 104 itself may shield the triple junction 110-1 from a higher voltage of the conductive structure 106. As a result, an electric field at the triple junction 110-1 may be relatively reduced. As will be described in further detail below, while the triple junction 110-1 may not be shielded by a coronal shield, in some embodiments, the conductive structure 104 may be electrically connected to a coronal shield configured to shield the triple junction 110-2. However, this coronal shield does not extend over the triple junction 110-1 such that it forms a coronal shield for that triple junction 110-1.

Furthermore, a portion 102-1 of the outer surface of the insulator 102 extends radially outward from the triple junction 110-1. Here, the portion 102-1 extends solely in a radial direction; however, in other embodiments, the portion may have an axial component. Regardless, as the conductive structure 106 is radially inward from the triple junction 110-1, the portion 102-1 extending radially outwards extends in a direction that has at least some component in a direction away from the conductive structure 106. As a result, any electrons generated at the triple junction 110-1 may be less likely to travel along the portion 102-1 of the outer surface of the insulator 102 and hence, less likely to cause an arc or a puncture of the insulator 102. In other words, the direction from the triple junction 110-1 along the portion 102-1 of the outer surface of the insulator 102 may not be a preferential direction for electrons.

In some embodiments, a thickness of the insulator 102 and, in particular, a thickness of the insulator 102 at the second end 102b may be relatively larger. For example, a thickness of the insulator at the second end 102b may be about 0.5 in. This thickness may be larger to increase the distance electrons must travel before the outer surface of the insulator 102 turns to extend towards the conductive structure 106.

The cross-section illustrated in FIG. 1 may be that of a wall of a conical insulator or a frustum insulator. The dashed line 107 represents an axis of the conical insulator or the frustum insulator. Accordingly, the conductive structure 104 is disposed on a radially interior surface of the insulator 102. As a result, at least part of the conductive structure 104 is surrounded by the insulator 102.

Figure 2:
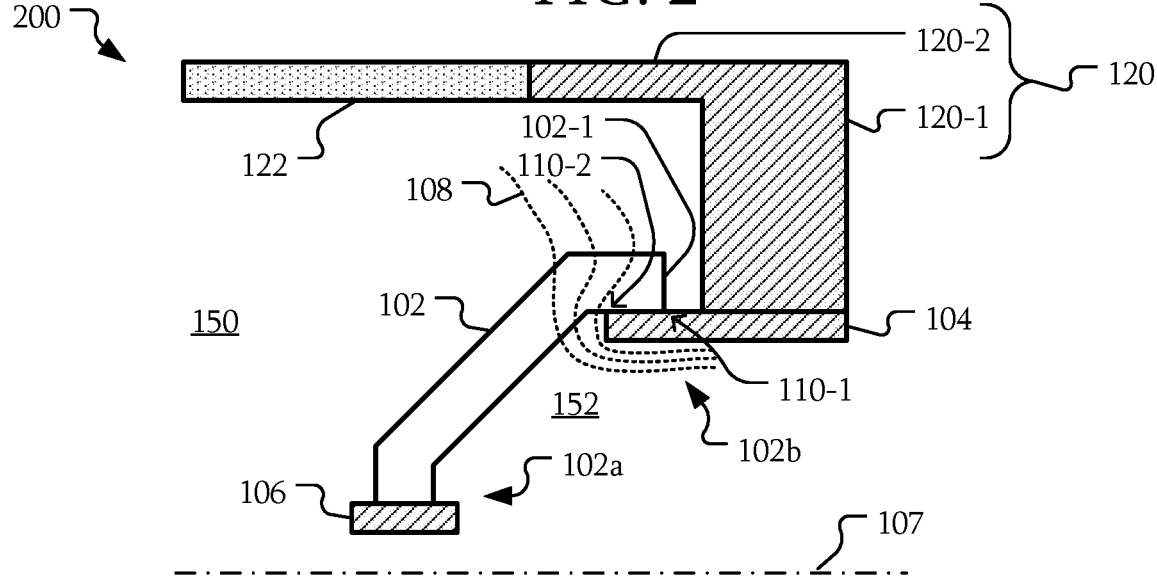
FIG. 2 is a cross-section of a wall of a high voltage structure with an example of an electric field according to some embodiments.

FIG. 2 is a cross-section of a wall of a high voltage structure with an example of an electric field according to some embodiments. The high voltage structure 200 may be similar to the high voltage structure 100 of FIG. 1 described above. However, in some embodiments, the high voltage structure 200 is electrically connected to a lead 120. The lead may include a conductive material, such as metal. The conductive material may have radiation shielding properties (e.g., lead [Pb]). The lead 120 includes a portion 120-1 extending radially from the conductive structure 104 and a portion 120-2 extending axially over the triple junction 110-1. Although the lead 120 and the conductive structure 104 are illustrated as separate structures that are connected, such as through soldering, welding, brazing, or the like, in other embodiments, the lead 120 and the conductive structure 104 may be a unitary structure. Moreover, in some embodiments, the lead 120 may be formed of separate components that are assembled together through soldering, welding, brazing, or the like.

The lead 120 is attached to a housing 122. The housing 122 may include litharge or other electrical insulating material. In particular, the housing 122 may include a material that has radiation shielding properties. The housing 122 may contain the medium 152 that contacts the outer surface of the insulator 102.

Three equipotential lines 108 are illustrated as an example of the electric field when a high voltage is applied to the conductive structure 106 and a lower voltage is applied to the conductive structure 104 and the lead 120. Each of these equipotential lines 108 represents a uniform step in voltage from the conductive structure 104 and/or the lead 120. While a higher electric field may exist on a radially inward side of the conductive structure 104, the electric field magnitude at the triple junction 110-1 is relatively lower as the change in potential over distance near the triple junction 110-1 is relatively lower.

While the electric field magnitude may be larger at the triple junction 110-2 than at the triple junction 110-1, the magnitude may still be relatively reduced. In particular, the portions 120-1 and 120-2 of the lead 120 reduce the magnitude of the electric field at the triple junction 110-2 by moving the equipotential lines further toward the conductive structure 106 and further away from the triple junction 110-2.

In some embodiments, the portion 102-1 of the outer surface of the insulator 102 follows a curve of equipotential or decreasing potential from the triple junction 110-1 when an electric field is formed between the conductive structure 104 and the conductive structure 106. Accordingly, any electrons generated at the triple junction 110-1 may be contained at the triple junction 110-1.

Figure 3:
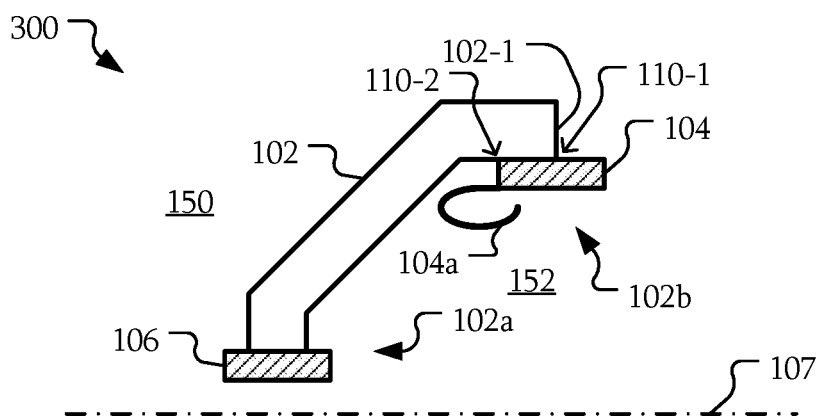
FIG. 3 is a cross-section of a wall of a high voltage structure with a coronal shield according to some embodiments.

FIG. 3 is a cross-section of a wall of a high voltage structure with a coronal shield according to some embodiments. The high voltage structure 300 may be similar to the high voltage structures 100 and 200 of FIGS. 1 and 2 described above. However, in some embodiments, the high voltage structure 300 includes a coronal shield 104a. In particular, the coronal shield 104a extends over the triple junction 110-2. Accordingly, the coronal shield 104a reduces a magnitude of the electric field at the triple junction 110-2. The coronal shield may include a conductive material, such as lead, nickel, steel, alloys of such materials or similar materials, or the like. In some embodiments, the material of the coronal shield 104a is the same as that of the conductive structure 104 while in other embodiments, the material is different.

As illustrated, the cross-section of the coronal shield 104a extends axially from a point on the conductive structure 104 that is offset from the triple junction 110-2. The coronal shield 104a extends in an open loop towards the conductive structure 106 before turning back towards the conductive structure 104. Although an open loop has been used as an example of a shape of the cross-section of the coronal shield 104a, in other embodiments, the shape may be different. Moreover, in other embodiments, the coronal shield 104a may have a solid cross-section.

Table 1 provides examples of electric fields at triple junctions (TD) in MV/m for triple junctions formed between an insulator, a seal ring, and oil on an outer surface or a vacuum on an inner surface of the insulator in various configurations. The first values are for a seal ring surrounding an insulator without a coronal shield. The next values are for a seal ring surrounding an insulator with a relatively small coronal shield extending over the outer medium triple junction. The next values are for a seal ring surrounding an insulator with a relatively large coronal shield extending over the outer medium triple junction. The final values are for a seal ring surrounded by an insulator with a coronal shield extending over the vacuum triple junction such as those described herein. As listed in Table 1, the electric field magnitude at the oil triple junction is smaller for an inner seal ring and an inner coronal shield than with the various configurations with an outer seal ring. In addition, the electric field magnitude at the vacuum triple junction is smaller than or similar to the magnitudes for the various configurations with an outer seal ring. Accordingly, using an inner seal ring as described herein may reduce the relative magnitude of the electric field at one or both of the triple junctions associated with the seal ring, reducing the chance of arcs or punctures.

TABLE 1

| TD Electric Field (MV/m) | Oil TD | Vacuum TD |
|---|---|---|
| Outer Seal Ring No Coronal Shield | 11.2 | 5.6 |
| Outer Seal Ring | 6.3 | 4.5 |

TABLE 1-continued

| TD Electric Field (MV/m) | Oil TD | Vacuum TD |
|---|---|---|
| Smaller Coronal Shield Outer Seal Ring | 2.8 | 2.9 |
| Larger Coronal Shield Inner Seal Ring Inner Coronal Shield (Vacuum TD) | 0.2 | 2.2 |

Figure 4:
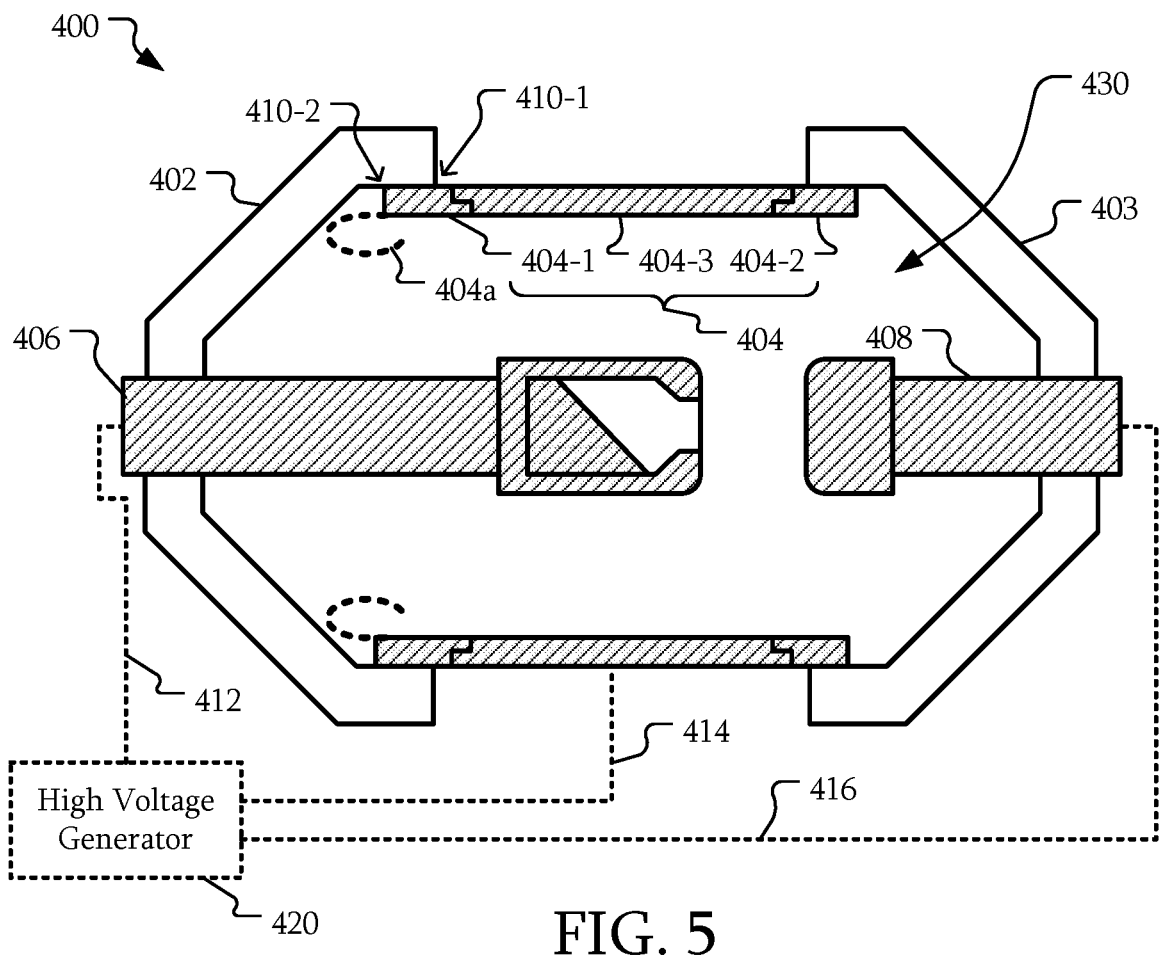
FIG. 4 is a cross-section of a high voltage structure having a vacuum chamber according to some embodiments.

FIG. 4 is a cross-section of a high voltage structure having a vacuum chamber according to some embodiments. The high voltage structure 400 may be similar to the high voltage structures 100, 200, and 300 described above. The high voltage structure 400 includes a vacuum chamber 430. The walls of the vacuum chamber 430 are formed at least in part by insulator 402, similar to the insulators 102 described above. An anode 406 penetrates the vacuum chamber. A conductive structure 404 is electrically insulated from the anode 406 by the insulator 402. A second insulator 403 insulates the cathode 408 from the conductive structure 404.

The conductive structure 404 includes seal rings 404-1 and 404-2 and a body 404-3. Each of the seal rings 404-1 and 404-2 may contact inner surfaces of the corresponding insulators 402 and 403. The body 404-3 may contact and be sealed to each of the seal rings 404-1 and 404-2. In other embodiments, the conductive structure 404 may be a unitary structure. The conductive structure 404 may also form at least part of a wall of the vacuum chamber 430.

Although the cathode 408, the anode 406, insulators 402 and 403, and the conductive structure 404 are illustrated in a particular configuration to form the vacuum chamber 430, additional conductive structures, insulators, or the like may be present and form part of the vacuum chamber 430. Moreover, although a particular type and configuration of the anode 406, the cathode 408, or the like has been used as an example, in other embodiments, the type and configuration may be different.

In some embodiments, the anode 406, conductive structure 404, and cathode 408 are electrically connected to a voltage generator 420. The voltage generator 420 is configured to generate one or more voltages that are applied to the anode 406, conductive structure 404, and cathode 408. For example, an anode voltage 412 may be about 160 kV. A conductive structure voltage 414 may be about 0 V. A cathode voltage 416 may be about −160 kV. Although particular voltages have been used as examples, in other embodiments, different voltages may be used. However, in some embodiments, where there is a relatively large voltage difference between a location of a triple junction and a location with a higher voltage, a conductive structure as part of a seal of the vacuum chamber 430 may be used as described herein to reduce electric fields at or near triple junctions associated with the seal. Although a conductive structure that is insulated from a conductive structure forming the anode 406 of the high voltage structure 400 has been used as an example, in other embodiments, the conductive structure having the higher voltage relative to the conductive structure 404 may be a different structure that is not electrically connected to the anode 406 but still has a relatively high voltage.

In some embodiments, a coronal shield 404a may be electrically connected to the conductive structure 404 such that the coronal shield extends over the triple junction 410-2 between the inner surface of the insulator 402, the conductive structure 404 and an interior of the vacuum chamber 430. In such a structure, the coronal shield 404a may be disposed within the vacuum chamber. The coronal shield 404a would thus be protected from damage during handling of the vacuum chamber. In contrast, if a coronal shield is disposed on the exterior of the vacuum chamber, the coronal shield may be scratched or otherwise damaged, reducing the performance of the coronal shield or causing the coronal shield to be replaced. Accordingly, using an inner conductive structure 406, such as one disposed on an inner seal ring, as described herein may eliminate a need for an outer coronal shield and any existing coronal shield 404a may be located in an interior of the vacuum chamber 430, reducing or eliminating the chance of damage to the coronal shield 404a.

Figure 5:
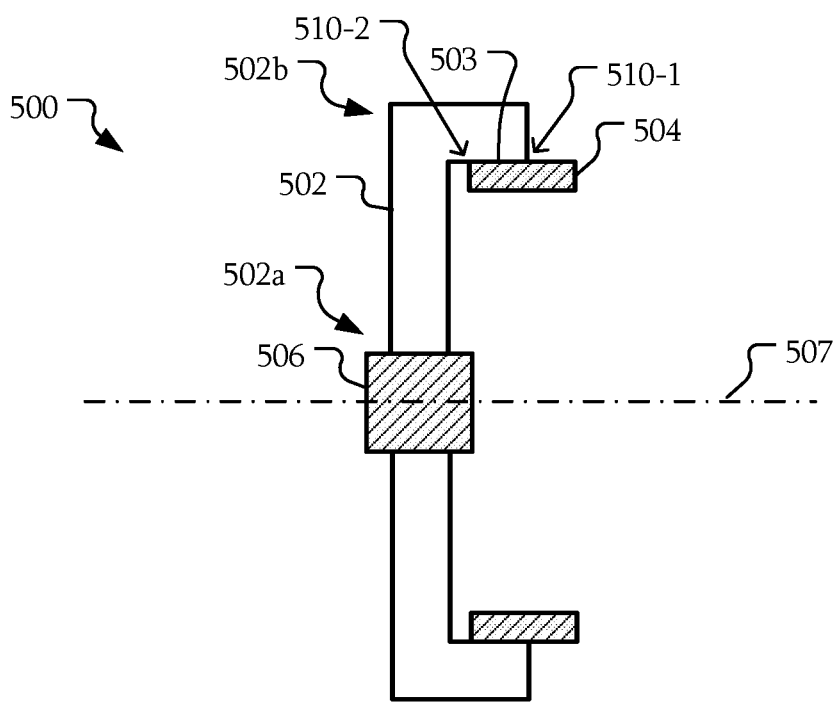
FIG. 5 is a cross-section of a wall of a high voltage structure according to some embodiments.

FIG. 5 is a cross-section of a wall of a high voltage structure according to some embodiments. The high voltage structure 500 includes an insulator 502 and conductive structures 504 and 506. These may be similar to the corresponding portions of the high voltage structures 100, 200, 300, and 400 described above. However, in some embodiments, the insulator 502 has a disc shape. The main body 502-1 may have a cylindrical shape with the diameter greater than the thickness. An axial protrusion 502-2 extends axially from the main body 502-1 creating a surface 503 that is radially inward facing. For example, the surface 503 may be parallel to the main axis 507 of the insulator 502. The conductive structure 504 may be attached to the insulator 502 in a similar manner to the conductive structures and insulators described above.

Similar to the high voltage structures 100, 200, 300, and 400 described above, two triple junctions 510-1 and 510-2 may be formed. These triple junctions 510-1 and 510-2 may have similar properties, such as the lower electric field magnitudes, as described above.

In some embodiments, having the conductive structures 104, 404, or 504 similar to those described above may improve manufacturability. For example, the insulator 104, 402, or 502 may be formed of ceramic and the conductive structure 104, 404, or 504 may be formed of a metal. The conductive structure 104, 404, or 504 may have a coefficient of expansion greater than that of the insulator 104, 402, or 502. As a result, at brazing temperatures, the metal may expand more than the ceramic causing compression on the braze joint. The compression will close the gap between the two, leading to braze joint with improved strength and quality.

Although the vacuum chamber 430 has been described above as being formed with high voltage structures similar to high voltage structures 100, 200, 300, and 400, in other embodiments the vacuum chamber 430 may be formed using high voltage structure 500 or similar structures.

Figure 6:
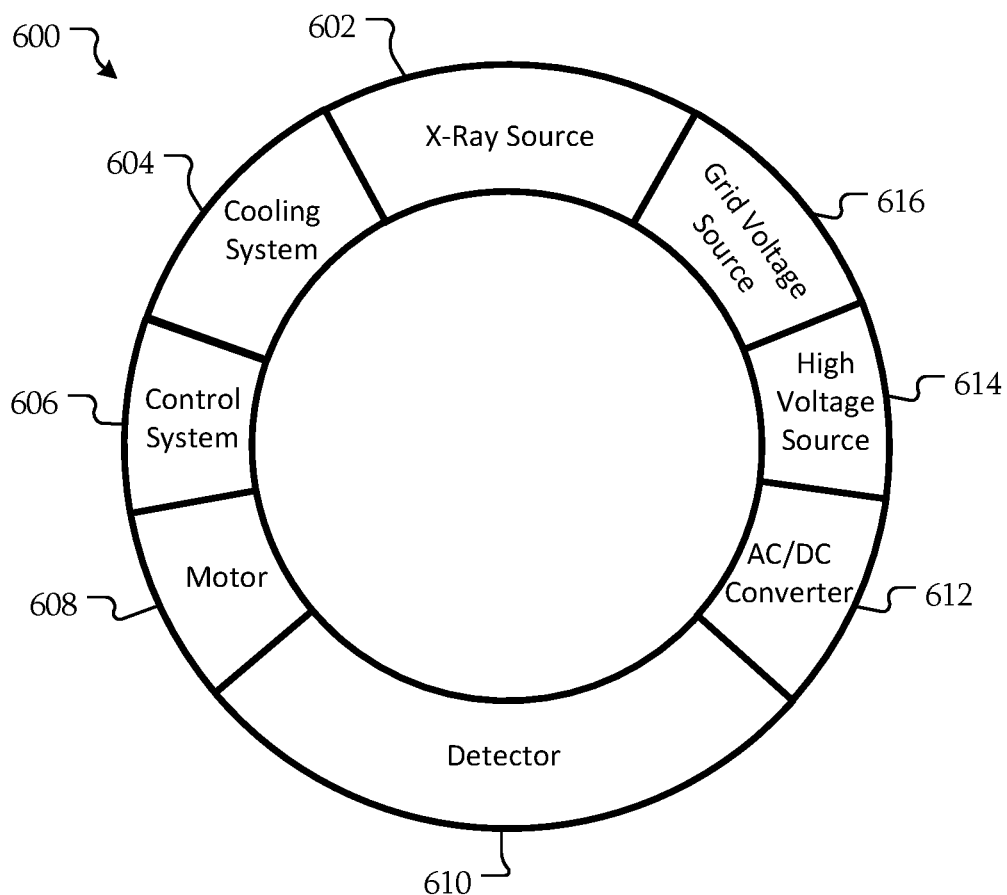
FIG. 6 is a block diagram of a computerized tomography (CT) gantry according to some embodiments.

FIG. 6 is a block diagram of a computerized tomography (CT) gantry according to some embodiments. In some embodiments, the CT gantry includes an x-ray source 602, a cooling system 604, a control system 606, a motor drive 608, a detector 610, an AC/DC converter 612, a high voltage source 614, and a grid voltage source 616. The x-ray source 602 may include a high voltage structure as described above. Although particular components have been used as examples of components that may be mounted on a CT gantry, in other embodiments, the other components may be different. Although a CT gantry is used as an example of a system that includes a high voltage structure as described herein, high voltage structure described herein may be used in other types of systems.

Figure 7:
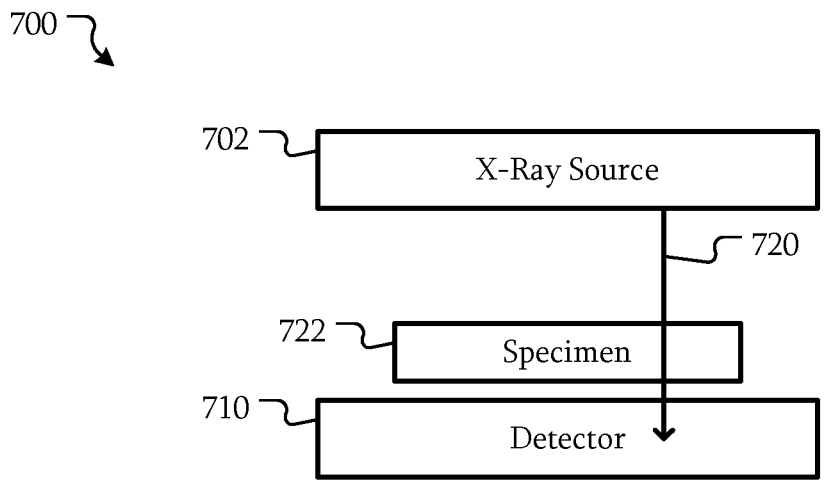
FIG. 7 is a block diagram of a 2D x-ray imaging system according to some embodiments.

FIG. 7 is a block diagram of a 2D x-ray imaging system according to some embodiments. The imaging system 700 includes an x-ray source 702 and a detector 710. The x-ray source 702 may include a high voltage structure as described above. The x-ray source 702 is disposed relative to the detector 710 such that x-rays 720 may be generated to pass through a specimen 722 and detected by the detector 710.

Referring to FIGS. 1-5, some embodiments include a structure, comprising: an insulator 102, 402, or 502 forming at least a part of a wall of a vacuum chamber, the insulator 102, 402, or 502 having a first end 102a, 402a, or 502a and a second end 102b, 402b, or 502b wider than the first end 102a, 402a, or 502a; a first conductive structure 106, 406, or 506 disposed at the first end 102a, 402a, or 502a of the insulator 102, 402, or 502; and a second conductive structure 104, 404, or 504 disposed at the second end 102b, 402b, or 502b of the insulator 102, 402, or 502, contacting the insulator 102, 402, or 502, and including at least a portion surrounded by the insulator 102, 402, or 502; wherein: a portion of an outer surface of the insulator 102, 402, or 502 extends radially outward from a triple junction 110-1, 410-1, or 510-1 between the insulator 102, 402, or 502, the second conductive structure 104, 404, or 504, and a medium 150 contacting the outer surface of the insulator 102, 402, or 502.

In some embodiments, the structure further comprises a coronal shield 104a or 404a extending from the second conductive structure over a triple junction 110-2, 410-2, or 510-2 between an inner surface of the insulator 102, 402, or 502, the second conductive structure 104, 404, or 504 and a medium 152 contacting the inner surface of the insulator 102, 402, or 502.

In some embodiments, a coronal shield 105 does not extend over the triple junction 110-1, 410-1, or 510-1.

In some embodiments, the second conductive structure 104, 404, or 504 is welded or brazed to the insulator 102, 402, or 502.

In some embodiments, the structure further comprises an anode 406; and a cathode 408; wherein the first end 102a, 402a, or 502a of the insulator 102, 402, or 502 is closer to the anode than the second end 102b, 402b, or 502b of the insulator 102, 402, or 502.

In some embodiments, the first conductive structure 106, 406, or 506 is electrically connected to the anode 406.

In some embodiments, the triple junction 110-1, 410-1, or 510-1 is a first triple junction 110-1, 410-1, or 510-1; and the first triple junction 110-1, 410-1, or 510-1 is further from the first end 102a, 402a, or 502a of the insulator 102, 402, or 502 than a second triple junction 110-2, 410-2, or 510-2 between an inner surface of the insulator 102, 402, or 502, the second conductive structure 104, 404, or 504 and a medium 152 contacting the inner surface of the insulator 102, 402, or 502.

In some embodiments the insulator 102 or 402 has a conical or a frustum shape.

In some embodiments, insulator 502 is a disc including an axial protrusion extending from the second end 502b of the insulator 502; and the second conductive structure 504 contacts the insulator 502 on a radially inward facing surface of the axial protrusion.

In some embodiments, the structure further comprises a voltage generator 420 configured to generate a first voltage 412 and a second voltage 414; wherein: the first conductive structure 106, 406, or 506 is electrically connected to the voltage generator 420 and configured to receive the first voltage 412; the second conductive structure 104, 404, or 504 is electrically connected to the voltage generator 420 and configured to receive the second voltage 414; and the first voltage 412 is higher than the second voltage 414.

In some embodiments, the portion of the outer surface of the insulator 102, 402, or 502 follows a curve of equipotential or decreasing potential from the triple junction 110-1, 410-1, or 510-1 when an electric field is formed between the first conductive structure 106, 406, or 506 and the second conductive structure 104, 404, or 504.

In some embodiments, the insulator 102 or 402 is a ceramic insulator having a conical or frustum shape; the portion of the second conductive structure 104 or 404 surrounded by the ceramic insulator includes a conductive ring contacting the ceramic insulator; and the second conductive structure 104, 404, or 504 includes a coronal shield 104a or 404a axially extending over a triple junction 110-1 or 410-1 between an inner surface of the ceramic insulator, the conductive ring, and a medium 152 contacting the inner surface of the ceramic insulator 102, 402, or 502.

Some embodiments include a structure, comprising: a vacuum chamber 430 including: an insulator 102, 402, or 502 forming at least part of a wall of the vacuum chamber 430; an anode penetrating the vacuum chamber 430; and a conductive structure 104, 404, or 504 insulated from the anode 406 by the insulator 102, 402, or 502, wherein the conductive structure 104, 404, or 504 is attached to the insulator 102, 402, or 502 on an inner surface of the insulator 102, 402, or 502.

In some embodiments, the insulator 102, 402, or 502 is a first insulator 102, 402, or 502; the vacuum chamber 430 further comprises: a cathode 408; and a second insulator 403; and the conductive structure 104, 404, or 504 is insulated from the cathode 408 by the second insulator 403.

In some embodiments, a portion of an outer surface of the insulator 102, 402, or 502 extends radially outward from a triple junction 110-1, 410-1, or 510-1 between the insulator 102, 402, or 502, the conductive structure 104, 404, or 504, and an exterior of the vacuum chamber 430.

In some embodiments, the structure further comprises a coronal shield 104a or 404a extending over a triple junction 110-1, 410-1, or 510-1 between the inner surface of the insulator 102, 402, or 502, the conductive structure 104, 404, or 504 and an interior of the vacuum chamber 430.

In some embodiments, a first triple junction 110-1, 410-1, or 510-1 is disposed between the inner surface of the insulator 102, 402, or 502, the conductive structure 104, 404, or 504 and an interior of the vacuum chamber 430; a second triple junction 110-1, 410-1, or 510-1 is disposed between an outer surface of the insulator 102, 402, or 502, the conductive structure 104, 404, or 504 and an exterior of the vacuum chamber 430; and the first triple junction 110-1, 410-1, or 510-1 is closer to the anode 406 than the second triple junction 110-1, 410-1, or 510-1.

In some embodiments, the structure further comprises a voltage generator 420 configured to generate a first voltage 412 and a second voltage 414; wherein: the anode 406 is electrically connected to the first voltage 412; the conductive structure 104, 404, or 504 is electrically connected to the second voltage 414; and the first voltage 412 is higher than the second voltage 414.

Some embodiments include a structure, comprising: first conductive means for generating x-rays in response to incident electrons; second conductive means; and insulating means for insulating the means for generating x-rays in response to incident electrons from the second conductive means and surrounding the second conductive means.

Examples of the first conductive means include the anode 406 described above.

Examples of the insulating means include the insulators 102, 402, and 502 described above.

Examples of the second conductive means include the conductive structures 104, 404, and 504 described above.

The first conductive means, the insulating means, and the second conductive means form a means for maintaining a high voltage difference. Examples of the means for maintaining a high voltage difference include the high voltage structures 100, 200, 300, 400, and 500 described above.

The means for maintaining a high voltage difference may be part of a means for maintaining a vacuum. Examples of the means for maintaining a vacuum include the high voltage structure 400.

In some embodiments the structure further comprises means for shielding a triple junction between the insulating means and the second conductive means. Examples of the means for shielding include the coronal shields 104a and 404a described above.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112 ¶6. Embodiments of the invention in which an exclusive property or privilege is claimed are defined as follows.

The invention claimed is:

1. A structure, comprising:
   an insulator forming at least a part of a wall of a vacuum chamber, the insulator having a first end with a first opening and a second end with a second opening wider than the first opening;
   a first conductive structure disposed at the first end of the insulator; and
   a second conductive structure disposed at the second end of the insulator, contacting the insulator, and including at least a portion surrounded by the insulator;
   wherein:
   a portion of an outer surface of the insulator extends radially outward from a first triple junction between the insulator, the second conductive structure, and a medium contacting the outer surface of the insulator; and
   the first triple junction is further from the first end of the insulator than a second triple junction between an inner surface of the insulator, the second conductive structure and a medium contacting the inner surface of the insulator.

2. The structure of claim 1, further comprising a coronal shield extending from the second conductive structure over the second triple junction.

3. The structure of claim 1, wherein a coronal shield does not extend over the first triple junction.

4. The structure of claim 1, wherein the second conductive structure is welded or brazed to the insulator.

5. The structure of claim 1, further comprising:
   an anode; and
   a cathode;
   wherein the first end of the insulator is closer to the anode than the second end of the insulator.

6. The structure of claim 5, wherein the first conductive structure is electrically connected to the anode.

7. The structure of claim 1, wherein the insulator has a conical or a frustum shape.

8. The structure of claim 1, wherein:
   insulator is a disc including an axial protrusion extending from the second end of the insulator; and
   the second conductive structure contacts the insulator on a radially inward facing surface of the axial protrusion.

9. The structure of claim 1, further comprising:
   a voltage generator configured to generate a first voltage and a second voltage;
   wherein:
      the first conductive structure is electrically connected to the voltage generator and configured to receive the first voltage;
      the second conductive structure is electrically connected to the voltage generator and configured to receive the second voltage; and
      the first voltage is higher than the second voltage.

10. The structure of claim 1, wherein the portion of the outer surface of the insulator follows a curve of equipotential or decreasing potential from the first triple junction when an electric field is formed between the first conductive structure and the second conductive structure.

11. The structure of claim 1, wherein:
   the insulator is a ceramic insulator having a conical or frustum shape;
   the portion of the second conductive structure surrounded by the ceramic insulator includes a conductive ring contacting the ceramic insulator; and
   the second conductive structure includes a coronal shield axially extending over the second triple junction where the second triple junction is disposed between an inner surface of the ceramic insulator, the conductive ring, and a medium contacting the inner surface of the ceramic insulator.

12. A structure, comprising:
    a vacuum chamber including:
       an insulator forming at least part of a wall of the vacuum chamber, the insulator including a first end with a first opening and a second end with a second opening wider than the first opening;
       an anode penetrating the vacuum chamber at the first end; and a conductive structure insulated from the anode by the insulator, wherein the conductive structure is attached to the insulator on an inner surface of the insulator at the second end and includes at least a portion surrounded by the insulators;

wherein:
- a first triple junction is disposed between the inner surface of the insulator, the conductive structure and an interior of the vacuum chamber;
- a second triple junction is disposed between an outer surface of the insulator, the conductive structure and an exterior of the vacuum chamber; and
- the first triple junction is closer to the anode penetration at the first end than the second triple junction.

13. The structure of claim 12, wherein:
the insulator is a first insulator;
the vacuum chamber further comprises:
- a cathode; and
- a second insulator; and the conductive structure is insulated from the cathode by the second insulator.

14. The structure of claim 12, wherein a portion of an outer surface of the insulator extends radially outward from the second triple junction.

15. The structure of claim 12, further comprising a coronal shield extending over the first triple junction.

16. The structure of claim 12, further comprising:
a voltage generator configured to generate a first voltage and a second voltage;

wherein:
- the anode is electrically connected to the first voltage;
- the conductive structure is electrically connected to the second voltage; and
- the first voltage is higher than the second voltage.

17. A structure, comprising:
means for maintaining a vacuum, including:
- first conductive means for generating x-rays in response to incident electrons;
- second conductive means; and
- insulating means for insulating the means for generating x-rays in response to incident electrons from the second conductive means and surrounding the second conductive means;

wherein:
- a first triple junction is disposed between an inner surface of the insulating means, the second conductive means and an interior of the means for maintaining the vacuum;
- a second triple junction is disposed between an outer surface of the insulating means, the second conductive means and an exterior of the means for maintaining the vacuum; and
- the first triple junction is closer to the first conductive means than the second triple junction.

18. The structure of claim 17, further comprising means for shielding the first triple junction.

* * * * *